(12) United States Patent
Patt et al.

(10) Patent No.: US 6,771,802 B1
(45) Date of Patent: Aug. 3, 2004

(54) METHOD AND APPARATUS FOR IMAGING AND LOCALIZING RADIATION

(75) Inventors: Bradley E. Patt, Sherman Oaks, CA (US); Jan S. Iwanczyk, Los Angeles, CA (US); Lawrence R. MacDonald, Los Angeles, CA (US)

(73) Assignee: Photon Imaging, Inc., Northridge, CA (US)

( * ) Notice: Subject to any disclaimer, the term of this patent is extended or adjusted under 35 U.S.C. 154(b) by 0 days.

(21) Appl. No.: 09/585,585

(22) Filed: Jun. 2, 2000

Related U.S. Application Data
(60) Provisional application No. 60/196,984, filed on Apr. 13, 2000.

(51) Int. Cl.[7] .................................................. G06K 9/00
(52) U.S. Cl. ......................... 382/128; 382/132; 378/140
(58) Field of Search ................................ 382/128, 129, 382/130, 131, 132; 250/536; 378/430, 2, 46, 90, 92, 98.4, 140; 600/407, 474, 410, 425, 436, 606, 430, 437

(56) References Cited

U.S. PATENT DOCUMENTS

| | | | | |
|---|---|---|---|---|
| 4,149,247 A | * | 4/1979 | Pavkovich et al. ............ | 378/14 |
| 4,344,440 A | * | 8/1982 | Aaby et al. ................... | 600/430 |
| 4,595,014 A | * | 6/1986 | Barrett et al. ................ | 600/431 |
| 4,889,991 A | * | 12/1989 | Ramsey et al. ........... | 250/336.1 |
| 5,591,974 A | * | 1/1997 | Troyer et al. ................ | 250/336 |
| 5,762,608 A | * | 6/1998 | Warne et al. ................ | 600/425 |
| 5,999,843 A | * | 12/1999 | Anbar ......................... | 600/474 |
| 6,118,892 A | * | 9/2000 | Williams .................... | 382/132 |

OTHER PUBLICATIONS

Alazraki, Naomi, Lymphoscintigraphy and the Intraoperative Gamma Probe, The Journal of Nuclear Medicine, vol. 36, No. 10, pp. 1780–1783, Atlanta, Georgia, Oct. 1995.

Alazraki, Naomi, et al., Lymphoscintigraphy, the Sentinel Node Concept, and the Intraoperative Gamma Probe in Melanoma, Breast Cancer, and Other Potential Cancers; Seminars in Nuclear Medicine, vol. 27, No. 1, pp. 55–67, Atlanta, Georgia, Jan. 1997.

(List continued on next page.)

*Primary Examiner*—Bhavesh M. Mehta
*Assistant Examiner*—Abolfazl Tabatabai
(74) *Attorney, Agent, or Firm*—Christie, Parker & Hale, LLP

(57) ABSTRACT

An imaging probe system includes a portable imaging gamma ray probe and a computer, and is used to locate and examine the distribution of radiation concentrated in animal tissue. The imaging probe system can operate in an imaging mode, a non-imaging mode (simple counting mode), or both simultaneously. The imaging probe system may include smart algorithms that analyze subdivisions of the images and indicate to the user via an audio indicator, a visual indicator, or both, the presence of one or more high-density concentrations of radiation within the image. The determination of such concentrations is governed either spatial resolution requirements of the subdivided image, or based on statistical variations of the cumulative number of particles detected. The imaging probe can also display the count of the detected radioactivity. The frequency of the audio output may be varied in proportion to the count rate and modulating the frequency, volume, phase or stereo panning of the audio output indicates the presence of more than one source in the field of view. By replacing the collimator of the imaging probe, the user is allowed to vary imaging parameters including variable spatial resolution, sensitivity and field of view.

54 Claims, 10 Drawing Sheets

OTHER PUBLICATIONS

Keshtgar, M., et al., The Sentinel Node in Surgical Oncology, pp. 1–78, Springer–Verlag Berlin Heidelberg, Germany, 1999.

Bongers, Vivian, et al., Towards Quality Assurance of the Sentinel Node Procedure in Malignant Melanoma Patients: A Single Institution Evaluation and a European Survey; European Journal of Nuclear Medicine, vol. 26, No. 2, pp. 84–90; Springer–Verlag, Feb. 1999.

Sandrucci, Sergio, et al., Sentinel Lymph Node Biopsy and Axillary Staging of T1–T2 N0 Breast Cancer: A Multicenter Study; Seminars in Surgical Oncology, 15, pp. 278–283, Wiley–Liss, Inc., 1998.

Schneebaum, Schlomo, et al., Clinical Applications of Gamma–Detection Probes–Radioguided Surgery, European Journal of Nuclear Medicine, vol. 26 (Supplement), pp. 526–535, Springer–Verlag, 1999.

De Cicco, Concetta, et al., Intraoperative Localization of the Sentinel Node in Breast Cancer: Technical Aspects of Lymphoscintigraphic Methods, Seminars in Surgical Oncology, 15, pp. 268–271, Wiley–Liss, Inc., 1998.

Borgstein, Paul, et al., Sentinel Lymph Node Biopsy in Breast Cancer: Guidelines and Pitfalls of Lymphoscintigraphy and Gamma Probe Detection, American College of Surgeons, vol. 186, No. 3, pp. 275–283, Mar. 1998.

Tiourina, Tatiana, et al., Evaluation of Surgical Gamma Probes for Radioguided Sentinel Node Localisation; European Journal of Nuclear Medicine, vol. 25, No. 9, pp. 1224–1231, Springer–Verlag, Sep. 1998.

* cited by examiner

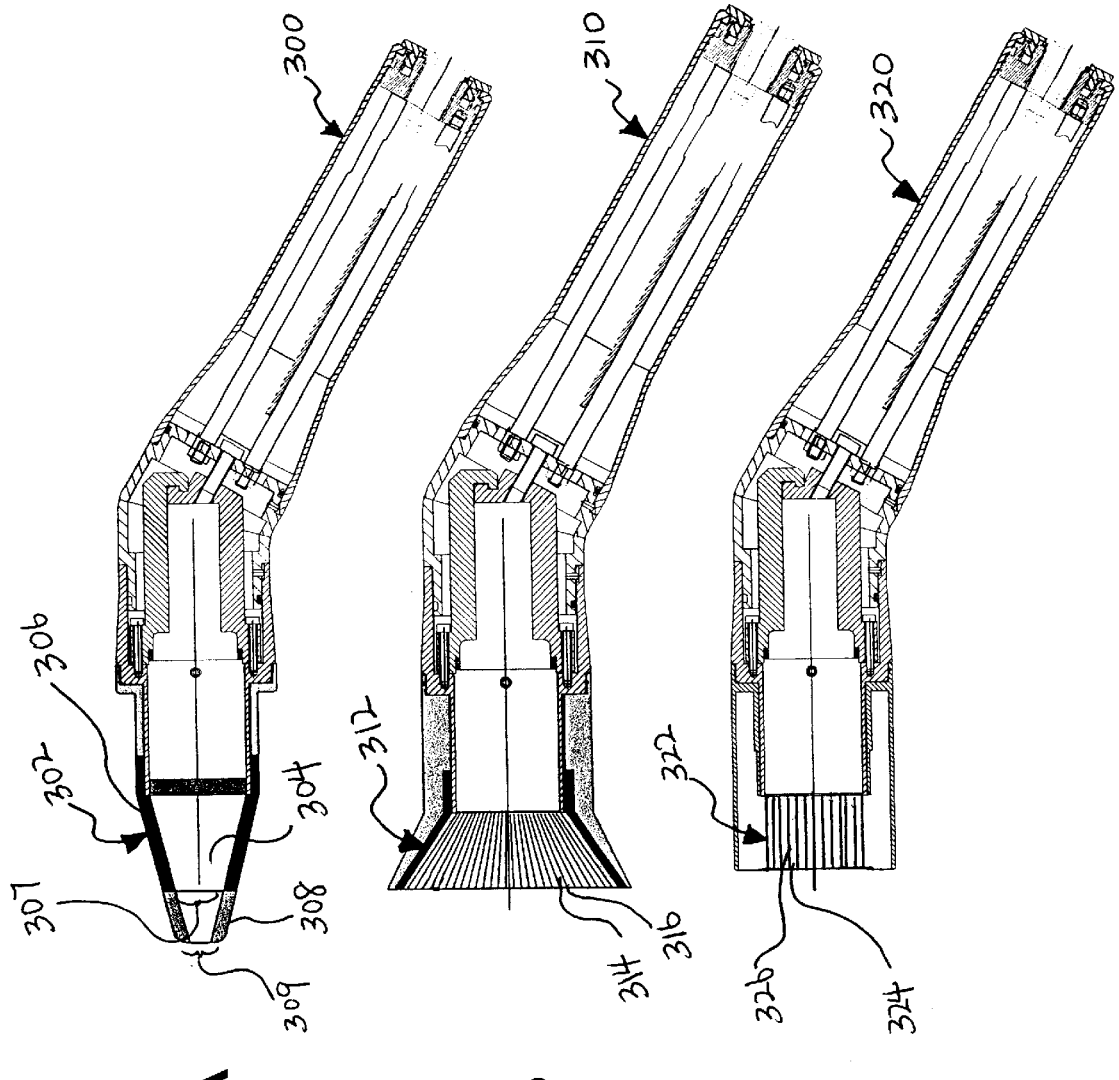

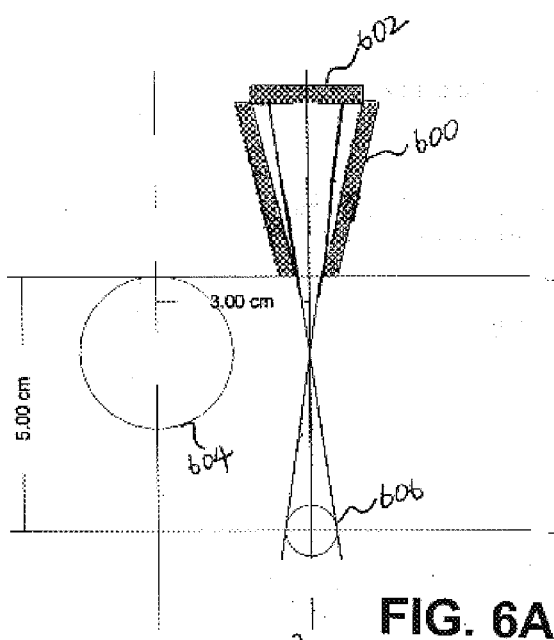 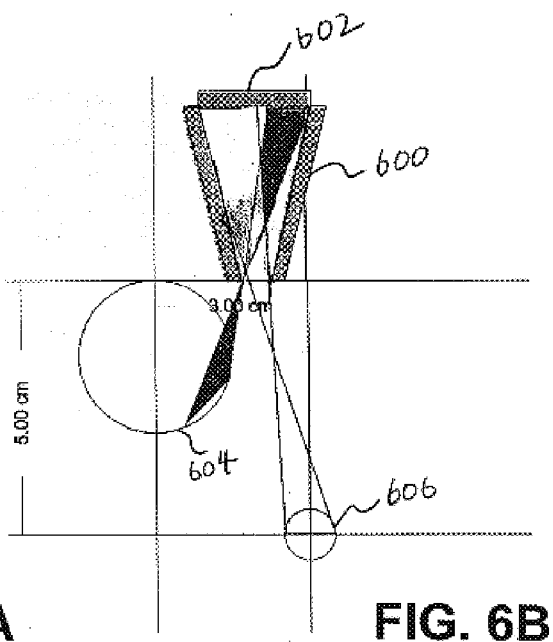
FIG. 6A    FIG. 6B
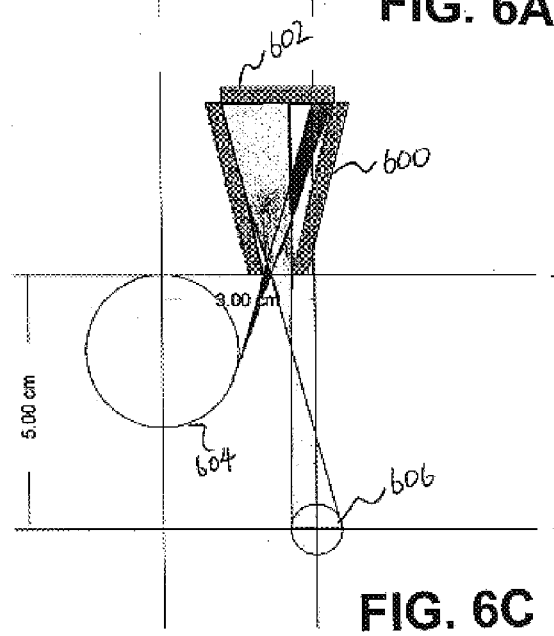 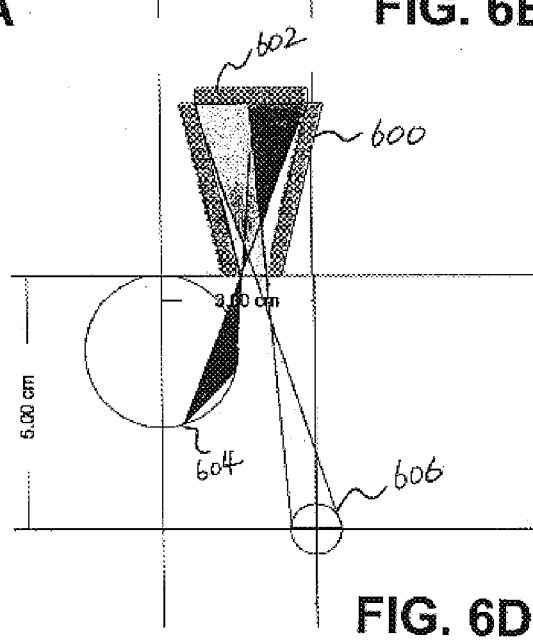
FIG. 6C    FIG. 6D

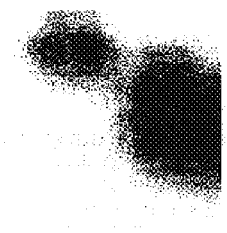
FIG. 8A
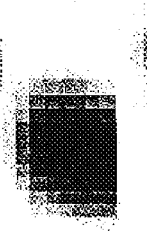
FIG. 8B  FIG. 8C
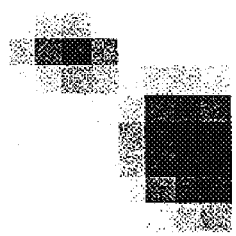
FIG. 8D
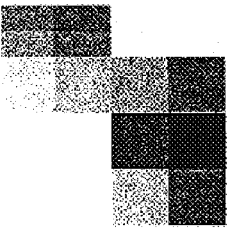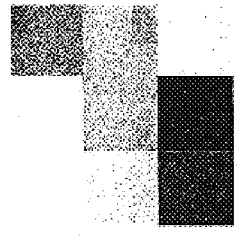
FIG. 8E  FIG. 8F  FIG. 8G

METHOD AND APPARATUS FOR IMAGING AND LOCALIZING RADIATION

CROSS REFERENCE TO RELATED APPLICATIONS

The present application claims priority under 35 U.S.C. § 119(e) to provisional Application No. 60/196,984 entitled "Radiation Imager and Localizer," filed Apr. 13, 2000, which is expressly incorporated herein by reference as though fully set forth.

STATEMENT REGARDING FEDERALLY SPONSORED RESEARCH OR DEVELOPMENT

This invention was made with government support under Small Business Innovation Research program (grant #1 R43 RR15157) awarded by the National Center for Research Resources of the National Institute of Health. The Government has certain rights in the invention.

BACKGROUND OF THE INVENTION

Gamma detection devices are used for locating radiation concentrated in animal tissue. The use of gamma detection devices is rapidly becoming the standard of care for surgical management of melanomas and increasingly for breast tumors. Gamma detection devices typically include standard (whole body) gamma cameras and hand-held non-imaging gamma detection probes, and are increasingly used for axillary staging in conjunction with removal of the primary tumor. Hand-held non-imaging gamma detection probes may also be referred to as non-imaging gamma detection probes, gamma probes, or non-imaging probes.

The presence or absence of regional lymph node involvement often determines the staging and treatment of malignant tumors. Lymphoscintigraphy, which typically allows monitoring of selected regional lymphatic drainage, is increasingly being used to determine which lymph node basins serve the diseased tissue, e.g., a tumor. During lymphoscintigraphy, a sentinel node concept is typically applied to estimate the extent to which a cancer has spread. The sentinel node concept is based on the observation that metastatic cancer cells travel primarily through lymph drainage to spread the cancer throughout the body. The sentinel node is defined to be the first lymph node downstream from the tumor.

Studies have indicated that, if there is no sign of malignancy in the sentinel node, the probability that cancer has spread is very low, and it is typically not necessary to remove the downstream lymph nodes, which had previously been a routine procedure during the treatment of breast cancer. The removal of downstream nodes (often more than 15 such nodes) has left many patients without adequate drainage for the lymph, and has led to serious edema and swelling, which often lasts many months to years. Thus, the use of the sentinel node concept to remove only the sentinel node typically reduces cost, morbidity and mortality, and provides equivalent or superior accuracy to axillary lymph node dissection.

In practice, a colloid labeled with $^{99m}Tc$ is generally injected in the region just outside the tumor, and a set of scintillation camera images are typically taken using a standard (whole body) gamma camera. These images typically show the migration of the colloid from the area of the tumor to the sentinel node and eventually to other nodes downstream from the tumor. Non-imaging gamma detection probes typically are then used at the time of surgery, both before and during the surgical process, to further localize the implicated nodes. The systems that include non-imaging gamma detection probes generally have an audio output that increases in sound level and/or frequency as the count rate of gamma rays increases. They may also display the number of gamma rays detected.

There are a number of shortcomings associated with using the non-imaging gamma detection probes. For example, the non-imaging system typically only registers the aggregate count rate and generally has no capability to distinguish localized concentrations of radiation from uniform ambient background, and typically has a very limited capability to distinguish between multiple local concentrations of radiation that are in proximity to one another. For another example, the non-imaging gamma detection probes typically are used to localize radiation to an area no smaller than its size, and thus the non-imaging gamma detection probes are typically kept relatively small to enhance their ability to localize radiation. Thus, it typically takes a long time to scan the area including the lymph basin and the area surrounding the injection.

Because of these and other shortcomings, there typically are a number of ambiguities associated with current modes of detecting the gamma ray or providing an output to indicate the detection. These ambiguities are typically associated with but not limited to: distinction between the injection site and nodes that are in proximity to the injection site; distinction between the sentinel node and secondary nodes; distinction of the sentinel node from activity along the path of migration of the injected colloid; and three-dimensional localization of the sentinel node.

Therefore, there is a need for a hand-held gamma detection probe that can reduce the ambiguities and facilitate the process of locating the sentinel node and distinguishing it from other sources of gamma ray radiation such as the injection site, other nodes, background, radiation due to scatter, etc.

SUMMARY OF THE INVENTION

One embodiment of the present invention is an imaging probe system for locating and examining the distribution of radiation concentration in animal tissue. The imaging probe system includes a portable imaging probe for detecting the distribution of radiation and a computer for processing the signal arising from the detected radiation. The imaging probe system also includes an audio output device that indicates the presence or absence of one or more radiation sources in the field of view (FOV) of the portable imaging probe. The frequency of the audio output may be varied in proportion to the count rate, and the modulation of the frequency, volume, and/or phase of the audio output also may indicate the presence of a focalized "hot spot" of radiation distinguishable from its surrounding, or more than one source in the FOV. The imaging probe system is also capable of providing images of gamma ray radiation distribution in the FOV with or without the audio output. The imaging probe system is capable of identifying and imaging gamma ray distributions both pre-operatively, e.g., for pre-surgical staging, as well as intra-operatively, e.g., in the operating room.

Another embodiment of the present invention is an imaging probe system having first and second portable imaging probes disposed one from the other at a known angle. The first and second portable imaging probes are used to generate X, Y and Z coordinates of a radioactive node. The X, Y and Z coordinates are used for three-dimensional localization of the radioactive node.

Yet another embodiment of the present invention is a portable imaging probe to assess a distribution of radiation concentrated in animal tissue. The portable imaging probe includes a collimator to direct rays of radiation such as gamma rays. The portable imaging probe also includes an imaging sensor to detect the rays of radiation. The imaging sensor can be a scintillator or it can be an energetic particle sensitive solid state detector. Different collimators with different aperture sizes, different number of chambers, and different chamber wall configuration, e.g., pin hole, diverging or parallel, can be used to vary spatial resolution, sensitivity and field of view.

Yet another embodiment of the present invention is a portable imaging probe that has a beta detection sensor in addition to a gamma detection sensor.

Yet another embodiment of the present invention is a method of assessing a distribution of radiation concentrated in animal tissue. The distribution of radiation is measured using a portable imaging probe. The measured distribution of radiation is processed to identify local concentrations of radiation. The local concentrations of radiation are indicated to the user through audio signals, images or a combination of the audio signals and images.

BRIEF DESCRIPTION OF THE DRAWINGS

FIG. 3A is a portable imaging probe with a collimator having a pinhole aperture with hole size ranging from a fraction of a millimeter up to the dimension of the scintillator crystal;

FIG. 3B is a portable imaging probe with a collimator having one or more chambers where the chambers are defined by one-dimensional or two-dimensional diverging chamber walls;

FIG. 3C is a portable imaging probe with a collimator having one or more chambers where the chambers are defined by parallel chamber walls;

FIGS. 6A–6D are a series of partial cross sectional views showing the gamma radiation incident on a portable imaging probe in one embodiment of the present invention, illustrating the projection of a small node and a large node (or injection site) onto the detector of the portable imaging probe as the portable imaging probe scans over the area containing the small node and the large node;

FIGS. 8A–8G illustrate a variable segmentation (8B–8G) of a typical image (8A) of two nodes acquired by a portable gamma detection imaging probe, the image being subdivided into 16×16, 15×15, 8×8, 5×5, 4×4 and 3×3 by integrating the counts in each subdivided region;

DETAILED DESCRIPTION

Figure 1:
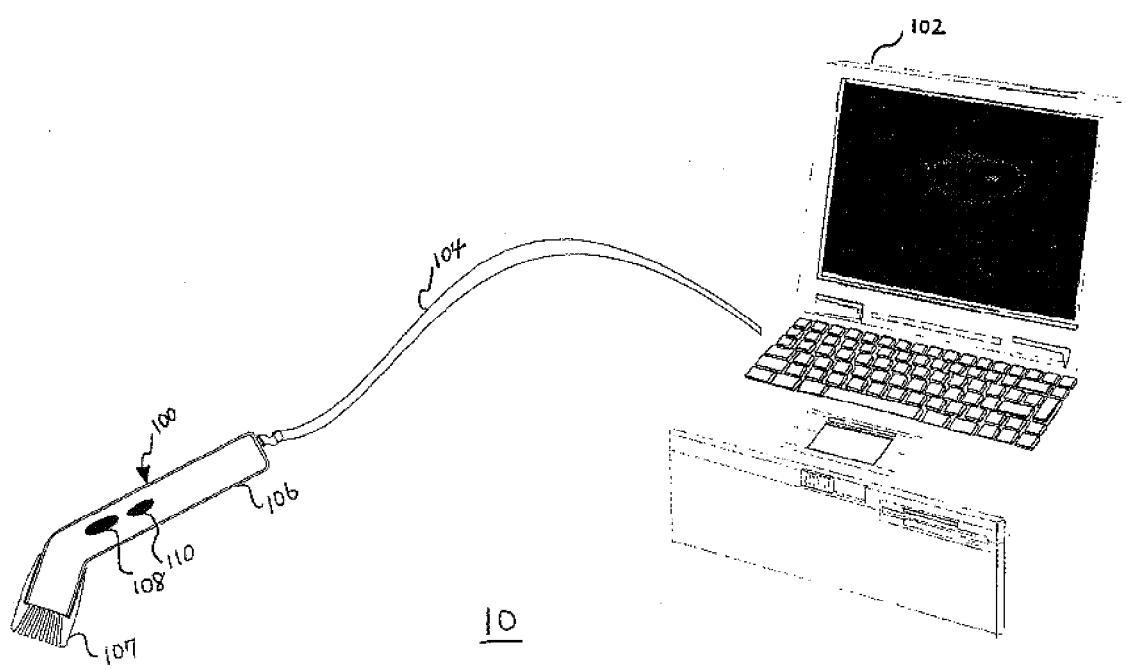
FIG. 1 is a view of an imaging probe system having a portable imaging probe and a computer connected via a cable.

The above and other features of the present invention may be more fully understood from the following detailed description, taken together with the accompanying drawings, wherein similar reference characters refer to similar elements throughout.

Referring now to the drawings, FIG. 1 is an imaging probe system 10 in one embodiment of the present invention. The imaging probe system 10 preferably includes a portable imaging probe 100, a computer 102 and a cable 104. The portable imaging probe 100 may also be referred to as an imaging probe, a hand-held imaging probe, a gamma detection imaging probe or a gamma camera. The portable imaging probe 100 preferably is coupled to a collimator 107, which is used to provide some directionality to detected radiation. The collimator 107 may have a collimation hole size that ranges from 25 mm down to 1 mm to improve the localization through a use of variable spatial resolution (coarse to fine).

The imaging probe system 10 in FIG. 1, by virtue of its imaging capability, is capable of removing several ambiguities associated with using a non-imaging probe during a sentinel node assessment procedure. In addition, the imaging probe system 10 is capable of alerting a user, e.g., a surgeon or a practitioner, of local concentrations of radiation through providing both the audio signals and images of the local concentrations of radiation. The imaging probe system 10 may utilize standard analysis and display software such as is commonly used in Nuclear Medicine acquisition and processing computers, and which is well known to those skilled in the art, including a "persistence" display that shows real-time images of between 0.1 and 60 seconds of accumulated image data.

In one embodiment of the imaging probe system 10, the user is able to alternate between imaging and cumulative counting modes with an actuation of a hardware or software switch. In another embodiment, the user is able to indicate both images and cumulative counts simultaneously through a combination of graphical presentation of the image data and audible indication of the gross counts. In yet another embodiment, the tone may be augmented through the use of software routines and algorithms, which analyze the data to indicate when there are single or multiple foci of radioactivity or sites of interest within the field of view. A single focus indicates a node distinguished from background. A site of interest may include a node as well as background. Multiple regions of interest indicate either the presence of a node near an injection site, or the presence of multiple nodes. Tone variations may indicate the presence of one or more focal regions of interest. In this case, an image can be displayed to assist the user in assessing the clinical situation.

The availability of the image reduces the time needed to make distinctions between the sentinel node and other radiation sources. Furthermore, imaging capability allows distinctions to be made that typically are very difficult when a non-imaging probe is used. For example, even when the sentinel node is in proximity to the injection site as to be typically indistinguishable using a non-imaging probe, the portable imaging probe 100 preferably allows the distinction to be made. In addition, the use of the portable imaging probe may obviate the need to use conventional whole body gamma cameras in a number of cases since the portable imaging probe may be used to follow the colloid from the injection site to the chain of lymph nodes that serve the tumor.

The portable imaging probe 100 may be held in hand or positioned using an articulating or stationary system. In one embodiment, the portable imaging probe 100 is connected via a cable 104 to the computer 102. The cable 104 may vary in length, e.g., from one foot to over 30 feet. In other embodiments, the portable imaging probe 100 may be coupled to the computer over a wireless communication medium.

The portable imaging probe 100 preferably includes a handle 106. The handle 106 preferably includes switches 108 and 110, which may be used to control one or more features of the imaging probe system or one or more parameters for data acquisition. In one embodiment, a first switch 108 preferably is used to toggle between an imaging mode, a non-imaging (e.g., audible tone representing count rate) mode and a dual imaging and audible tone mode. A second switch 110 preferably is used to start, stop, pause, resume and clear an acquisition. The function of the switches may also be controlled from the computer 102. The switches may also have other functions and/or the handle 106 may include switches for other functions.

The computer 102 may be a personal computer, a Nuclear Medicine workstation, a mainframe computer or any other suitable computer. For example, the computer 102 may be a workstation, a laptop, a palmtop, a personal computer or a terminal of another computer, and may run on one or more operating systems such as Windows 95/98, Windows NT, UNIX, LINUX, MS-DOS, or any other suitable operating system.

The computer 102 preferably incorporates capabilities for controlling data acquisition, processing the acquired data, generating and displaying images based on the acquired data, and manipulating the images. The computer 102 may also have capabilities to share the acquired data using internal or external storage means or network connections. In addition, the computer 102 may have capabilities to provide printed output of the images. Further, the computer 102 may be used to catalog the images.

The computer 102 preferably has capabilities for processing audible sounds representing features of the images such as integrated gross counts, count rate, number of areas with count rates above the background count rate, and other features pertinent to the localization and display of radionuclide distributions in animal tissues.

The computer 102 may also be able to provide a numerical display of the number of radiation particles counted, the counting time, the rate at which particles are being counted and these same quantities for previously acquired, independent images. In addition, applicable statistical parameters associated with each quantity may also be displayed simultaneously.

Figure 2:
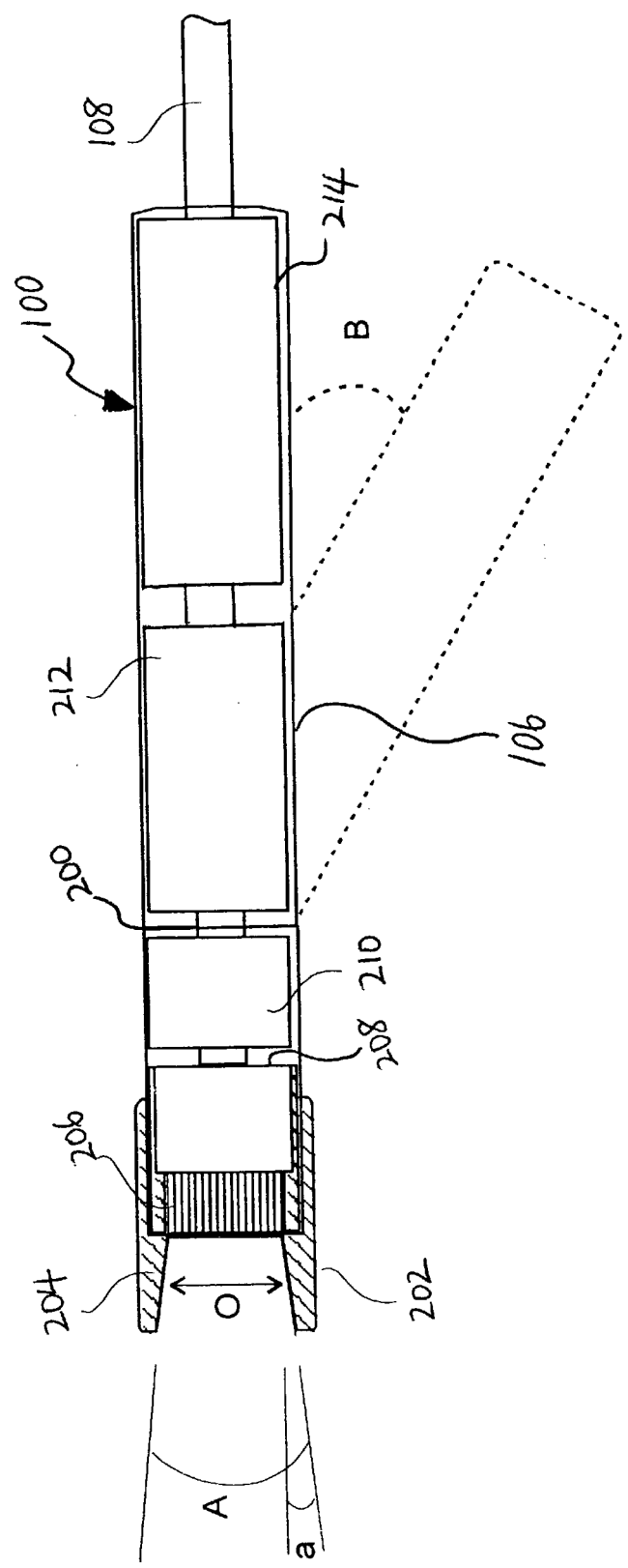
FIG. 2 is a cross sectional view of a portable imaging probe (hand-held-imaging camera) including a scintillator, a position sensitive photomultiplier tube (PS-PMT) and processing electronics housed in an inert packaging.

FIG. 2 is a cross sectional view of a portable imaging probe 100 in one embodiment of the present invention. The portable imaging probe 100 preferably includes a collimator 202 and a scintillator 206. The collimator 202, which may also be referred to as a collimator sheath, preferably provides shielding against background radiation and collimation of the source radiation towards the scintillator 206. The collimator 202 preferably includes a shielding portion 204. The shielding portion 204 preferably reduces septal penetration of radioactivity. The scintillator 206 may include a single scintillation crystal or it may include an array of scintillation crystals. The scintillator 206 preferably generates light upon detection of radioactivity, e.g., gamma rays.

The scintillator 206 preferably is coupled to a detector unit 208. The detector unit 208 may include a position sensitive photomultiplier tube (PS-PMT), a solid-state photodetector such as a silicon PIN diode, or it may include any other suitable detector. The detector unit 208 preferably receives the light, i.e., photons, generated by the scintillator 206 and generates electrical signals. The electrical signals preferably contain image data of the detected radiation.

In one embodiment, the detector unit 208 preferably has an intrinsic spatial resolution of 0.1 mm to 3.5 mm. Detector units in other embodiments may have different intrinsic spatial resolutions. The detector unit 208 may also be suitable x-ray, gamma ray, or other energetic particle sensitive detectors such as those employing solid state materials including Cadmium Telluride (CdTe), Mercuric Iodide (HgI2), CZT, silicon and others. The scintillator 206 may not be needed when the detector unit 208 includes an x-ray, gamma ray, or other energetic particle sensitive detector. The detector unit 208 may also include both a gamma ray detector and a particle sensitive detector.

The electrical signals from the detector unit 208 preferably are processed by an amplifier 212 or amplifiers (not shown) and a signal shaper 214 or signal shapers (not shown) to generate the image data including position and energy signals. The image data preferably is provided to analog-to-digital converters (ADCs) on the processing circuitry (not shown). In one embodiment, the processing circuitry resides in a computer, such as the computer 102 in FIG. 1. Buffers or line drivers (not shown) preferably are used to drive the signals including the image data to be provided over a long distance, e.g., 1 ft to 30 ft., over a cable 108 to the computer 102 where they may be further processed, e.g., by the processing circuitry. In other embodiments, a wireless transmitter may be used to transmit the signals to a receiver, which, e.g., may be on a computer. In other embodiments, the processing circuitry may be a part of the portable imaging probe 100.

The portable imaging probe 100 preferably also includes a DC-to-DC converter 210. The DC-to-DC converter preferably converts the power input voltage to a voltage used by the detector portion of the portable imaging probe 100. For example, the DC-to-DC converter may convert +12V input voltage to −800V used to bias the PS-PMT included in the detector unit 208.

One or more of the scintillator 206, the detector unit 208, the DC-to-DC converter 210, the signal amplifier 212 and the signal shaper 214 may be packaged in a housing 200. The housing 200 may be made of an inert metal or plastic package appropriate for intra-operative use. For example, in one embodiment of the present invention, the housing 200 is an inert stainless steel packaging. The handle 106 may be straight or angled at an angle B. For example, the angle B may range from zero degrees to 90 degrees in one embodiment. The angling of the handle 106 preferably enhances operator comfort during the sentinel node procedure. For example, the handle may include neoprene or other soft grips and/or the grip may be made less slippery.

In one embodiment, the collimator 202, which may also be referred to as a collimator sheath, may include single or multiple holes, O, with hole sizes ranging from 0.5 mm up to the dimension of the scintillator crystal. In other embodiments, each of the holes may be smaller than 0.5 mm or larger than the dimension of the scintillator crystal. The angle A of the opening O in the described embodiment may range, e.g. from −60 degrees with respect to the direction normal to a detection surface of the scintillator up to +60 degrees. The collimator 202 in FIG. 2 is diverging at the opening O, forming an angle a with respect to the direction normal to the detection surface of the scintillator. In other embodiments, walls of the collimator may coverage to form, e.g., a single pinhole opening. Additional shielding may be incorporated into the area adjacent to but outside of the collimator and/or the area adjacent to but outside of the scintillator.

Each of the FIGS. 3A, 3B and 3C is a cross sectional view of a portable imaging probe in one embodiment of the present invention. They are representative only as they merely describe exemplary embodiments of the invention. Other suitable structures for practicing the invention may be employed and will be readily apparent to persons of ordinary skill in the art. The portable imaging probes 300, 310 and 320 include collimators 302, 312 and 322, respectively.

Each of the collimators 302, 312 and 322 has one or more chambers, e.g., 304, 314 and 324 defined by chamber walls 306, 316 and 326, respectively. For example, the collimator 302 in FIG. 3A has only one chamber 304, which is accessible through a single pinhole opening 307. On the other hand, the collimators 312 and 322 include multiple chambers. Each of the chambers is a segregated pathway of radioactivity from a respective opening to the scintillator.

The chamber walls 306, 316 and 326 preferably are constructed of material having a high atomic number, such as tungsten, tantalum or lead in order to limit septal penetration. Radiation incident on a chamber wall is typically absorbed by the chamber wall before it passes through to an adjacent chamber. Thus, the chamber walls help to ensure that only radiation which comes directly into an opening at one end of a chamber and which is propagated in a direction substantially parallel to the chamber walls or of lessor angle exits the other end of the chamber to the detector, e.g., scintillator. In one embodiment of the present invention, each of the chambers corresponds to a size matched scintillator segment in a coupled scintillator array, and therefore, to a pixel in a raw image (unprocessed image) contained in the image data. In other words, there is one-to-one correspondence between the chambers, the crystal segments and the resulting image, and the pixels. For example, the collimator with 32×32 chambers, coupled to a 32-by-32 scintillator array, would be used to generate a raw image having 32×32 pixels.

The collimator 302 shown in FIG. 3A includes the pinhole aperture 307. The pinhole aperture 307 may have a hole size ranging from a fraction of a millimeter up to the dimensions of the scintillator crystal used in the portable imaging probe 300. An extension 308 with a pinhole 309 may be coupled to the collimator to increase resolution of the raw image. The collimator 312 in FIG. 3B includes chamber walls which diverges in at least one of horizontal and vertical directions. The chamber walls in the collimator 312 of FIG. 3B may also diverge in both directions. The collimator 322 in FIG. 3C includes multiple parallel hole apertures. Each of the parallel hole apertures lead to a segregated chamber, e.g., the chamber 324. The chamber walls, e.g., the chamber walls 326, are substantially parallel to one another.

Figure 4C:
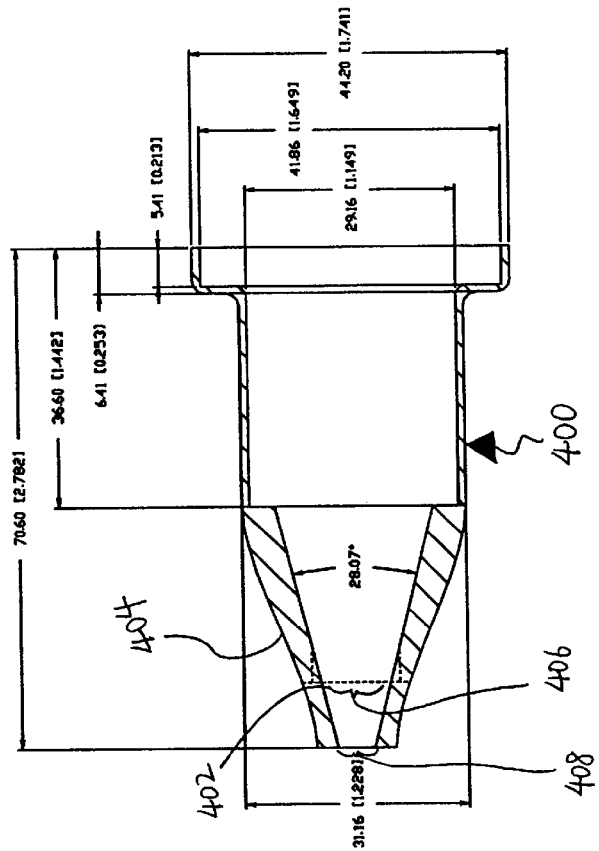
FIGS. 4A–4C are a 3-D view, a top view and a cross sectional view of a collimator having a pin hole and an extension.
Figure 4A:
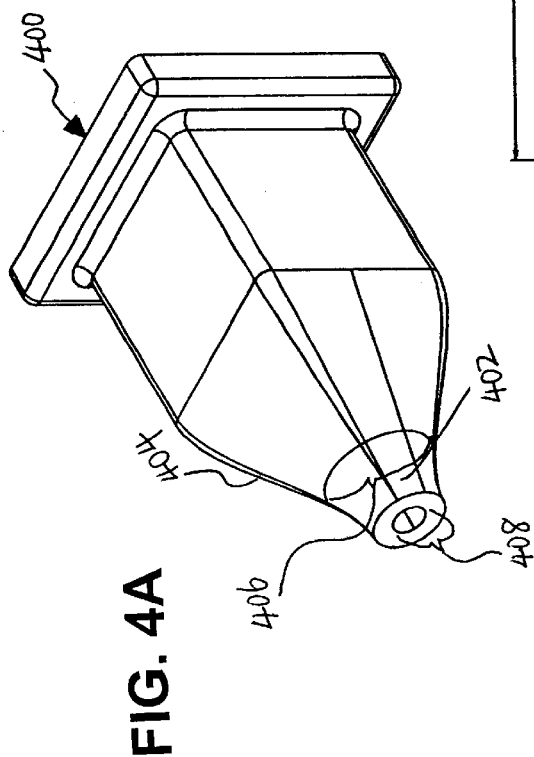
Figure 4B:
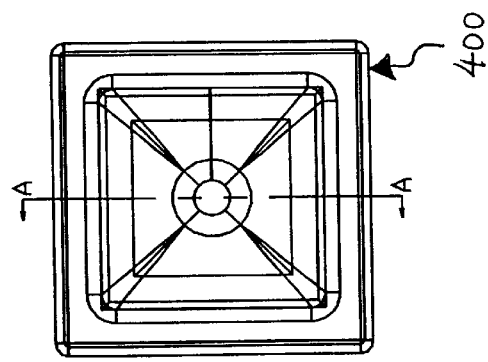

FIG. 4A is a three dimensional view of a collimator 400 having a pinhole aperture 406. The collimator 400 generally allows for a coarse imaging capability but a high sensitivity. In one embodiment, the pinhole 406 includes a threaded portion (not shown) about the aperture 406. A pinhole insert 402, which may also be referred to as an extension, may be coupled to the threaded portion to result in smaller aperture diameter to provide images having a higher resolution. For example, the aperture 408 of the extension 402 is smaller than the pinhole aperture 406, and therefore the extension 402 allows for higher resolution of a resulting image. However, when the aperture of the collimator 400 is made smaller using the extension 402, sensitivity of the portable imaging probe coupled to the collimator 400 is typically reduced. FIGS. 4B and 4C are a top view and a cross sectional view of the collimator 400, respectively.

Figures 5A, 5B, 5C:
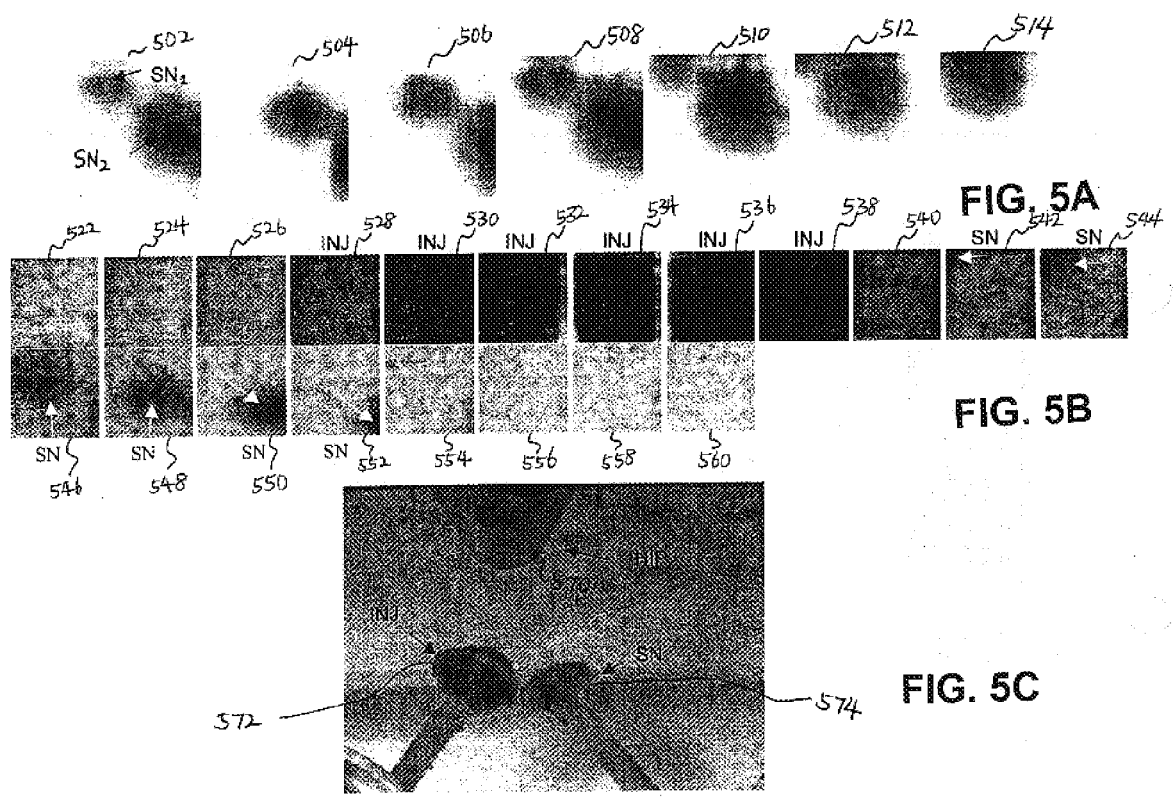
FIG. 5A is a set of scintillation camera images of two closely situated sentinel nodes $SN_1$ and $SN_2$.
FIG. 5B is a set of scintillation camera images of a simulated sentinel node (SN) positioned 3 cm from a simulated injection site (INJ)
FIG. 5C is a test set up, such as the one used to take the sequences of scintillation camera images 5A and 5B showing relative positions of a hand-held (portable) imaging probe (HIP), a simulated injection site (INJ) and a simulated sentinel node (SN)

FIG. 5A is a sequence of simulated scintillation camera images for a simulated sentinel node ($SN_1$) near a second simulated sentinel node ($SN_2$). In FIG. 5A, $SN_1$ is relatively distinguishable from $SN_2$ using the imaging capability of the present invention. $SN_1$ may not be distinguishable from $SN_2$ with a non-imaging probe. FIG. 5B is a sequence of simulated scintillation camera images of a simulated SN near a simulated INJ. In FIG. 5B, the SN has significantly lower concentration of radioactivity (e.g., by a factor of 10–50) than the INJ. Thus, it is very difficult to identify or locate the SN with a non-imaging probe. FIG. 5C is a set up that shows relative locations between simulated INJ 572, simulated SN's 574 and HIP 570. The set up in FIG. 5C may be used to take a sequence of simulated scintillation camera images similar to FIGS. 5A and 5B.

Each of FIGS. 6A–6D is a partial cross-sectional view of a collimator 600 and a detector 602 in one embodiment of the present invention. The detector 602 may include a scintillation crystal or it may include an array of scintillation crystals. The detector 602 may also include a solid state detector such as a detector based on CdTe, HgIz, CZT, etc. The collimator 600 may be an integral part of a portable imaging probe. The collimator 600 may also be detachable from the portable imaging probe. The collimator 600 preferably is shaped so that all of a projected image entering the collimator is captured by the detector 602.

FIGS. 6A–6D show two distinct nodes of radiation, one large node 604 and one small node 606. The arrangement of nodes 604 and 606 shown in FIG. 6A is a typical arrangement encountered when searching for a sentinel lymph node during a staging procedure. The large node 604 may represent an injection site of a radioactive agent and the small node 604 may represent a nearby lymph node. FIGS. 6A–6D illustrate the collimator 600 and thus the portable imaging probe, at different locations with respect to the two nodes at four specific points during a scan.

In FIG. 6A, the small node 606 is within the field of view (FOV) of the detector 602 but the large node 604 is not within the FOV. In FIG. 6A, the projection of the small node 606 is smaller than the size of the detector 602. Since the projection of the small node 606 onto the detector 602 is smaller than the size of the detector 602, the response of the detector 602 typically shows certain areas of high density counting rate (the projection of the small node onto the detector) and other areas of low density counting rate (the area of the detector not projected upon by the node) by virtue of its imaging capability. From the audio or visual output of the imaging probe system, existence of distinct high density and low density regions within the FOV may be determined. A non-imaging probe may be able to register the count rate but typically cannot register the existence of distinct high and low density regions within the FOV.

In FIGS. 6B and 6C, the detector 602 is situated such that at least a portion of both the large node 604 and the small node 606 is within the FOV of the detector 602. FIGS. 6B and 6C show that the projections of the large node 604 and the small node 606 onto the detector 602 are separated by a region that does not subtend either the large node 604 or the small node 606. The region between where the large node 604 and the small node 606 project onto the detector 602 typically registers a low count rate density. The regions where the large node 604 and the small node 606 project onto the detector 602 typically register relatively higher count densities. The identification of distinct count density regions by virtue of the imaging capability and smart algorithms described herein provide information to the user via either an audio indicator, a visual indicator, or both simultaneously. A non-imaging probe typically would not register the existence of two distinct regions of high count density, but rather would generally register only the sum of the densities.

FIG. 6D is an illustration of the case where the projections of the large node 604 and the small node 606 onto the detector 602 overlap onto the detector 602. In this case, there typically is no low density count rate region between the projections on the detector 602. However, by virtue of its imaging capability, the imaging probe system is typically capable of distinguishing between the regions where only the large node 604 projects onto the detector 602 and where only the small node 606 projects onto the detector 602.

This differentiation is possible for nodes with different size, different depths, different activity, or a combination of these differences. In lymph node staging procedures, the injection site typically tends to be larger, and it generally contains more activity, and is typically at a different depth than the nodes that are the subject of the search, e.g., the sentinel node. The smart algorithms identify that there are two regions within the FOV that have differing count rate densities and convey that fact to the user, e.g., a surgeon or a practitioner, with an audible indication, a visual indication, or both.

Figure 7:
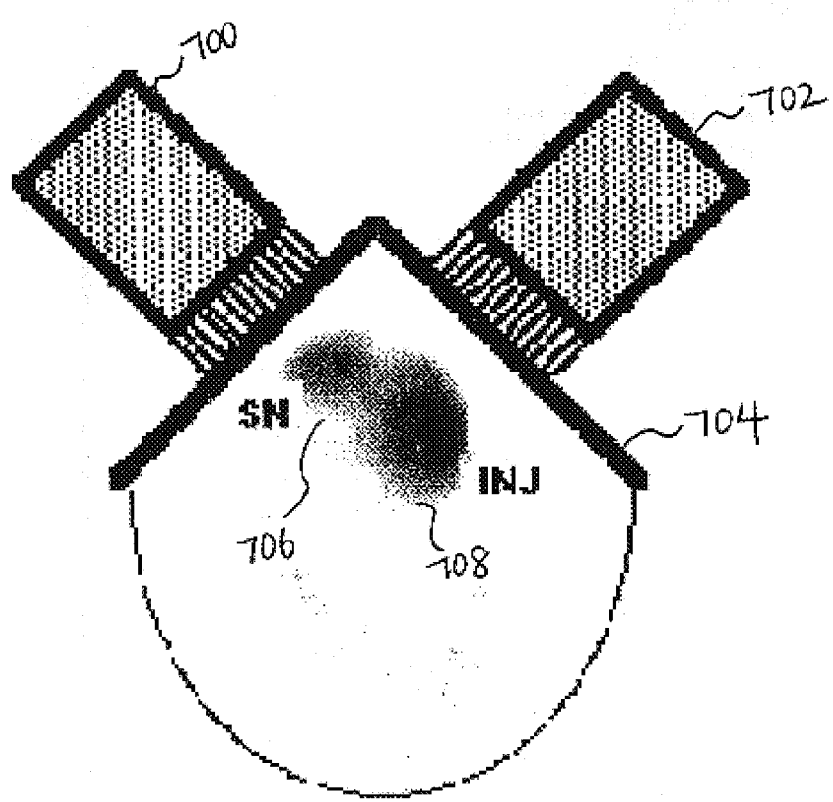
FIG. 7 is an illustration that shows an accomplishment of three-dimensional localization of a radioactive node by acquiring two different images from two different views, each view from a a different portable imaging probe, such that the first imaging probe is disposed at a fixed known angle from the second probe. The use of such gives the X, Y and Z coordinates of the node.

FIG. 7 is an illustration that shows a use of two portable imaging probes to generate a 3-D image of a node. In FIG. 7, the portable imaging probes 700 and 702 are coupled to a fixture 704. The portable imaging probes 700 and 702 are substantially perpendicular to one another. Using the 3-D image, the portable imaging probe may also be used to guide fine needle aspiration (fna) biopsy. The 3-D image may be used for precise fine needle placement to extract tissue samples for histology or complete removal of the node. Since the sentinel node may be removed using the fna biopsy, a standard surgical procedure may not be needed. The use of this less-invasive procedure may result in a great reduction in cost and trauma to the patient.

A three-dimensional localization of concentrations of radiation is generated by acquiring images with the portable imaging probe at two different views. The three-dimensional information preferably is used to guide a needle directly to the node of interest, e.g., a sentinel node (SN) 706 to collect a tissue sample for histology or complete removal of the node. In one embodiment, a source of radiation may be attached to the end of the needle, making the needle visible on the image generated by the portable imaging probes.

Using the method of the described embodiment, the accuracy of the needle placement may be enhanced by labeling the needle with a radioactive isotope.

In another embodiment, markings may be made on the skin of the patient to reference the X-Y-Z position of the node of interest. The markings preferably are made immediately after acquiring the images from two different views and identifying X-Y-Z via the images. The spatial resolution of the portable imaging probe, which may be better than 1 mm in one embodiment typically depends on such conditions as the collimator selected, imaging conditions, and the immediate temporal vicinity of the measurements. The use of portable imaging probes typically results in more accurate delineation of the node than is possible with non-imaging probes.

The imaging probe system in one embodiment of the present invention preferably uses smart algorithms based on statistical techniques, which are based on the nature of radioactive decay. The decay of a radioactive nucleus may be thought of as a binary process, i.e. it either decays or it does not. This kind of process (like flipping a coin or rolling a dice) typically follows a binomial distribution. The binomial distribution describes the probability of measuring a certain outcome (say, flipping "heads") that has a certain probability of occurring (probability of "heads" is 50%) When the probability of occurrence is very low, as it is in nuclear decay, then the binomial distribution is typically well approximated by the Poisson distribution. (Of a collection of a very large number of nuclei, only a very small number of them decay, making the probability of decay of a given nucleus very low.)

The Poisson probability distribution is given by $P(x)=m^x e^{-m}/x!$

In this equation: P(x) is the probability of measuring x (e.g. a radioactive decay); m is the mean value of x; and e is the base of the natural logarithm (ln(e)=1, e=2.71828 . . . ) The predicted variance of the distribution is given by m, the mean value, and the standard deviation, σ, is the square root of the variance, σ=√m. It is this predicted standard deviation that is typically used to calculate fractional errors in the measurements made with the portable imaging probes. Full descriptions of the binomial distribution and the Poisson distribution can be found in W. Feller, *An Introduction to Probability Theory and Its Applications*, $2^{nd}$ ed., Wiley, New York, 1957.

An algorithm may be used in the imaging probe system of the present invention to calculate the total count rate by integrating the data over all pixels (i.e. all triggers to the ADC) for a fixed time, e.g., time between $1/1000^{th}$ of a second and 10 seconds. The user preferably has an option to make calculations either based on spatial resolution requirements or based on counting statistics requirements. The statistical requirements typically depend on the level of accuracy desired.

In one embodiment of the present invention, a fast (<1 second) decision preferably is as to whether one or more sources are present. This decision typically requires the ability to discern peaks (areas with high count density) that are sufficiently greater than the valleys (areas with low count density). It typically does not require accurate reporting of the absolute count densities in those areas. Thus for such a decision, large errors (up to 20% or more) may be tolerated. Then when an area with a single distinct peak or multiple peaks has been determined, one embodiment of the present invention notifies the user who can then hold the portable imaging probe in place for several seconds (or minutes) to obtain a highly accurate recording of the distribution of radioactivity in the field of view. (FOV)

In one embodiment, the user may set a limit on how coarse an image subdivision may be. The algorithm may then subdivide the image up to, but not more than, the specified limit. In each subdivision, the algorithm preferably also searches along profiles of the subdivided image for peaks and valleys. The profiles may be the rows or columns of the subdivided image or combinations of adjacent rows and columns. The profiles may also be one or more lines at any angle (not necessarily horizontal rows or vertical columns).

The algorithm preferably interprets peaks in the profiles as regions of high density counting of gamma rays and valleys as regions of low density counting of the gamma rays. Associated with the peaks and valleys are the integral number of detected gamma rays from which the standard error of the mean is calculated using Poisson counting statistics. The algorithm uses the low count density region as a baseline and calculates the error in the high count density region above the baseline value. The algorithm reports the resulting number of high density regions and low density regions along with their corresponding Poisson mean standard errors. The reporting methods may include an audio signal variation or a display of the values on a monitor. The reporting methods may also include any other suitable methods of reporting.

In another embodiment, the user may set a limit on an acceptable standard error of the mean as calculated from Poisson statistics. In this case, a first subroutine of the algorithm preferably calculates the number of times the image may be subdivided and still yield counting statistics within the limit preset by the user, e.g., a surgeon or a practitioner. The first subroutine preferably subdivides the image to the maximum allowed by the statistical constraint. Meanwhile, a second subroutine of the algorithm preferably analyzes the profiles for peaks and valleys. The results are reported in the same way as described for the first case. In a third case, the system preferably uses a default acceptable standard error between 1% and 30%. Larger errors may be tolerable under certain conditions.

The FIGS. 8A–8G are related to the interpretation of the images obtained by the imaging probe system in one embodiment of the present invention. In the described embodiment, a portable imaging probe preferably contains a position sensitive radiation detector that generates images with a basic pixel size. The image may be square (N by N pixels); it may also be rectangular (N by M pixels where N is not equal to M); circular (N pixel diameter); elliptical (N pixel major axis and M pixel minor axis); or have other shapes. The basic pixel size may be dictated by the embodiment of the detector or it may be determined in the software algorithm used to generate the image.

The image may include a gray-scale image and/or a color-scale image. The intensity of the image preferably represent a presence of radiation. In the described embodiment of the imaging probe system, the basic pixel size preferably is dictated by the size of the discrete radiation detectors, e.g., an array of scintillation crystals coupled to a position sensitive photomultiplier tube (PS-PMT). In other embodiments, the discrete radiation detectors may be coupled to an array of solid-state detector pixels, such as silicon PIN diodes or silicon drift detectors, which are either coupled to scintillation crystals or are sensitive to direct absorption of energetic radiation such as x-rays, gamma-rays, beta rays, alpha rays, neutrons, or any other suitable sub-atomic particles.

In other embodiments, the radiation detector may include a single continuous scintillation crystal, or other phosphorus material sensitive to energetic radiation, coupled to position sensitive photo-sensors. A continuous radiation detector may also include a continuous material that is sensitive to the absorption of energetic radiation, such as complex semiconductor compounds Codemium Telluride (CdTe), Mercury Iodide (HgI2), CZT or others. The signal in the continuous absorption material is shared between one or more of position sensitive sensors below the continuous material. In the case of shared signals from a continuous material, the basic pixel size may be determined by an image-generating algorithm.

The algorithms preferably include statistical evaluations of the electronic signals generated in the position sensitive sensors that yield the most probable location of the absorbed particle. In one embodiment, the algorithms preferably include the weighted mean algorithm whereby the location of the absorption is given by the first moment of the electronic signals from the position sensitive sensor relative to a fixed axis. In another embodiment, the algorithms include locating the absorption at the position such that the integral sum of the electronic signals are equal on either side of said position. In other embodiments the statistical weighting algorithms may include the weighted mean algorithm and the integral sum algorithm, and utilize thresholding of signal values and non-linear weighting terms.

In general, fully pixelated images include an ordered matrix of the basic pixels, each basic pixel containing the number of absorbed particles in the position of the corresponding basic pixel. The value in each basic pixel is generally altered to correct for non-uniformity in the detector system. In addition, the value in each basic pixel is generally altered in accordance with values in a suitable number of surrounding pixels in order to generate an overall image that preferably appears smooth to visual observation. The images ultimately displayed are typically enlarged from the matrix of basic pixels to a size suitable for viewing by a person. The enlargement process utilizes smoothing techniques such as pixel replication, linear interpolation, nearest neighbor smoothing and/or non-linear convolutions such as a cubic spline interpolation.

In one embodiment of the present invention, novel analysis algorithms that evaluate the distribution of radiation source within the FOV of the camera are used. The novel analysis algorithms include analyses of the data after subdividing the image to varying degrees in a process which may also be referred to as a variable segmentation. The subdivided images may include any number of regions between and including two and the fully pixelated image as illustrated in FIG. 8A The image is typically subdivided into even squares such as 4 subdivisions (2×2), 9 subdivisions (3×3) (FIG. 8G), 16 subdivisions (4×4) (FIG. 8F), 25 subdivisions (5×5) (FIG. 8E), 64 subdivisions (8×8) (FIG. 8D), 225 subdivisions (15×15) (FIG. 8C), 64 subdivisions (16×16) (FIG. 8B), etc. with equal size subdivisions. Irregular subdivisions with unequal subdivision sizes may also be made.

A computer processor typically generates the subdivided images by integrating the values in neighboring pixels. For example, a (128×128) pixel image may be re-segmented into a 64 pixel-by-64 pixel image by combining adjacent (2×2) pixel regions of the original (128×128) pixel image into a single pixel of the resulting (64×64) pixel image. A (32×32) pixel image may similarly be generated by performing a similar (2×2) combination of the (64×64) pixel image. This process may be continued until only a single pixel remains.

The analysis algorithms evaluate the segmented images along the rows and columns, which may also be referred to as profiles, of the subdivisions. Distinct concentrations of radiation are identified by the computer processor if it determines that there are regions of high numbers of detected particles separated by regions of low numbers of detected particles. The separation of densely populated regions and sparsely populated regions may be across profiles of any of the subdivisions of the fully pixelated image.

The profiles include rows or columns of the subdivided image, or combinations of adjacent rows and columns, or a combination of one or more lines at any angle (not necessarily horizontal rows or vertical columns). The profiles preferably are evaluated for peaks and valleys. Peaks typically represent dense concentrations of radiation and valleys typically represent sparse concentrations of radiation. The analysis algorithms include: differentiation of the profiles to determine extreme values in the profiles and the rate of change of the concentration; double differentiation to identify the extreme values as peaks or valleys; peak-to-valley ratios; integral counts in peak and valley regions, and other calculations to establish with specified statistical certainty the existence of distinct regions of high concentrations of radioactivity. The degree of subdivision, i.e., segmentation, used to search for distinct regions may be preset to a default, user selectable or set at a standard based on the total number of decays detected.

The statistical requirements preferably depend on the level of accuracy desired. In one embodiment of the present invention, the requirements include making a fast (<1 second) decision as to whether there are one or more sources present. This decision typically requires the ability to discern peaks (areas with high count density) that are sufficiently greater than the valleys (areas with low count density). It typically does not require accurate reporting of the absolute count densities in those areas. Thus for such a decision, large errors (up to 20% or more) may be tolerated. Then when an area of a single peak distinct from a surrounding background level or multiple peaks has been determined, the described embodiment of the present invention notifies the user, who may then hold the portable imaging probe in place for an interval of seconds to minutes to obtain a highly accurate recording of the distribution of radioactivity in the field of view.

A radioactive material decays in accordance with Poisson process whose standard error of the mean is typically given by the square-root of the number of measured decays. During a procedure using the described embodiment, statistics may be derived and presented that represent the minimum fractional errors that can be expected due to Poisson counting statistics. For a given image acquisition, the numbers of detected particles in each subdivision is typically greater when there a fewer subdivision regions.

In one embodiment, the searches for distinct concentrations of radiation preferably are conducted by subdividing the image so that the standard error due to Poisson statistics is at a fixed level. In this case, an image would not be subdivided to a larger number of subdivisions if the standard error in the dense region(s) rose above the preset level.

In another embodiment, the number of subdivisions may be preset and regions searched within the preset subdivided image. In this case, the standard error preferably is calculated by the processor and displayed for the user's information. From the value of the displayed standard error, the user can interpret the reliability of the distinction of the dense regions. Or the user may wait at the position of interest for an accumulation of detected particles that increases the accuracy of the counting statistics. Application and camera specific errors preferably are also incorporated through empirical evaluations of the camera. These additional factors are typically due to imperfect side shielding and effects unique to each collimator. As an example of the variation of statistical accuracy with subdivision size, Table 1 lists counting rates required for certain statistical accuracy in the case of different subdivisions of the images. The table assumes images are integrated for 0.5 seconds as an example. Image integration time may be changed by the user from 1 millisecond to several tens of seconds. The table further assumes equal counts in each subdivision (i.e., a uniform image).

TABLE 1: Minimum number of counts per second to allow the given number of subdivisions for a ½ second integration period and specified error.

|  | Acceptable Error | | | |
| --- | --- | --- | --- | --- |
| Subdivisions | 1% | 10% | 20% | 30% |
| 4 × 4 | 320,000 | 3,200 | 800 | 355.52 |
| 8 × 8 | 1,280,000 | 12,800 | 3,200 | 1,422.08 |
| 16 × 16 | 5,120,000 | 51,200 | 12,800 | 5,688.32 |

The computer may display the imaging results in a variety of formats including choice of image color tables, image thresholding, image filtering, an audible output proportional to the frequency of gamma-ray detections, etc. The task of switching between imaging mode and simple counting may be achieved via a switch on the handle of the portable imaging probe or via the computer console (keyboard, touch-screen, mouse). All parameters given in counting mode (e.g. the count rate and/or accumulated counts as a function of time) may be displayed during imaging mode. However, different collimators may be appropriate for different methods of using the portable imaging probe and may yield different spatial resolution, sensitivity and statistical results.

Figure 9:
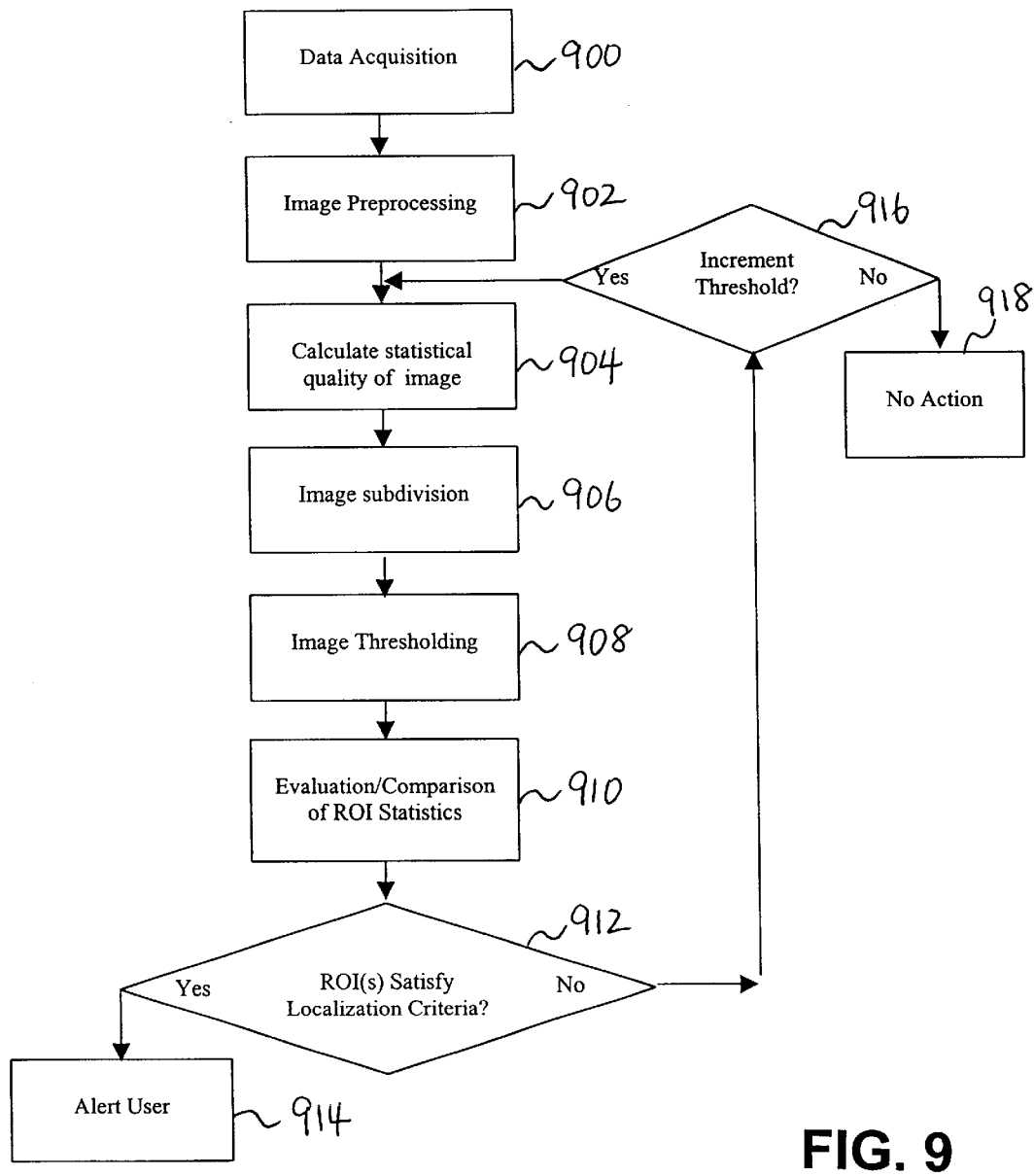
FIG. 9 is a flow diagram illustrating an algorithm for automatic identification of local concentration of radiation.

FIG. 9 is a flow diagram illustrating an algorithm for automatic identification of local concentrations of radiation in one embodiment of the present invention. Using the algorithm of FIG. 9, Regions of Interest (ROIs) within the images that represent local concentrations of radioactivity are automatically identified. For the purposes of this application, an "activity" within ROI or elsewhere refers to one or more of the following: the number of detected gamma rays; the average number of detected gamma rays; the number of detected gamma rays per second; and the average of the rate of gamma ray detection per second.

Input parameters to the process of automatic identification of local concentrations may include but are not limited to: 1) image acquisition time per frame (typically between 10 msec and several seconds, preferably between 200 milliseconds and 1 sec.); 2) maximum or minimum image subdivision (typically from 2×2 to 256×256). The highest resolution is 512 by 512, the lowest is 2 by 2 and a typical resolution is between 2 by 2 and 32 by 32; 3) maximum or minimum standard error expressed as:
 a) The mean variance (standard deviation) of the ROI activity;
 b) Ratio of the activity (peak or mean) in the ROI to that in the background (mean or standard deviation);
 c) Combination of the above two parameters; and
 d) Activity threshold levels for ROI identification.

In step 900 of the flow diagram in FIG. 9, data preferably is acquired. A portable imaging probe in one embodiment of the present invention preferably includes a collimator, such as a collimator 400 in FIG. 4 for example. The collimator preferably focuses (or directs) gamma rays from radionuclides distributed in the observed area within the field of view (FOV) onto a scintillator or any other suitable sensor such as a solid state sensor. The scintillator typically includes one or more scintillator crystals. A scintillator crystal typically includes materials such as NaI[Tl], CsI[Na], CsI[Tl], LSO, BGO or other suitable materials.

The scintillator typically converts the incoming gamma ray energy into light. The light from the gamma rays preferably propagates to a position sensitive photomultiplier tube (PS-PMT) or an array of PS-PMTs, or to an array of photomultiplier tubes (PMTs) or other photodetector with spatial resolving capability, which converts the light energy into electrical signals, which typically include image data. In one embodiment, the array of PMTs includes substantially identical PMTs. In other embodiments, the arrays of PMTs may include one or more different types of PMTs. The processing circuitry, e.g., readout circuitry and software, preferably are used to acquire the image data thus produced. The processing circuitry may reside in the portable imaging probe or in the computer. The processing circuitry may also be distributed between the portable imaging probe and the computer. Thus, in the described embodiment, the image data preferably are acquired through the use of the portable imaging probe and stored in the computer memory or any other storage medium.

In step 902 the image data preferably are processed into an image using an Anger logic. The Anger logic is described in detail in an article, Anger, HO "Scintillation Camera," Rev. Sci. Instr. 29, 27. (1958), and is well known to those skilled in the art. The Anger logic is a standard way of decoding information in gamma cameras, and is used to calculate the interaction position between two or more points of measurement in a similar manner as a triangulation or an interpolation scheme.

Using the Anger logic, a raw image with the maximum detector resolution (between 8×8 and 128×128, typically 16 by 16 or 32 by 32) preferably is generated. The raw image preferably is processed to generate a suitable representative image using a combination of processing tools. The processing tools may include but are not limited to tools for: (1) expanding the image to a greater number of pixels using interpolation or other expansion algorithms; (2) smoothing the image using spatial or frequency domain methods; (3) filtering the image using spatial or frequency domain methods; (4) enhancing the image contrast by applying methods; and (5) reducing the noise in the image.

In Step 904, the data in the image preferably is analyzed to determine the statistical quality of the image. The statistical quality calculation may include but is not limited to: determination of the total counts in the image; determination of the counts in regions of the image; comparison of the counts in regions of the image with the average counts in the image; and extraction of 1st, 2nd, or higher moments (mean, standard deviation, etc.) in the image or its sub regions.

In step 906, from the representative image, a lower resolution image preferably is generated by methods including integration, wavelet transform, frequency domain filtering, etc. The resolution to which the image is reduced preferably is determined on the basis of either preset default parameters or based on calculated parameters in the image such as its statistical quality, or based on user specified parameters that restrict the image subdivision by spatial and/or activity constraints.

In step 908, ROIs preferably are identified in the subdivided image through various pattern recognition algorithms. A primary example is the selection of pixels in the subdivided image that exceed a predetermined fraction of the maximum activity level. For example, in one embodiment, the predetermined fraction may be ⅓ (of the maximum activity level). Analysis of the profiles of the subdivided image preferably is also used to qualify ROIs. Peak-to-valley ratios and the slopes of the profiles at the peaks preferably are used to accomplish the analysis of the ROI.

Once the ROI(s) have been identified, they preferably are analyzed in Step 910 through a qualification process to ascertain if a true localized region of concentrated radioactivity exists. These analyses include the image profile properties mentioned above and statistical techniques. The statistical techniques are based on the Poisson probability distribution. The criteria for qualification of the ROIs may include but are not limited to:

a) standard deviation of the activity below a predetermined value (e.g. 10% or 30%, to be empirically determined); and b) ratio of ROI activity to background activity above a predetermined value (e.g. 2:1 ratio, to be empirically determined).

c) ratio of the ROI activity (either peak value in the ROI or average value in the ROI) to the standard deviation of the background activity above a preset value (e.g., a 3:1 ratio implies a "signal to noise ratio" value of 3σ, which represents a certainty of 99.7% for the existence of the peak).

The "background" activity to which the ROI activity is compared may consist of the entire image, or the entire image not including the ROI, or a regional background only in the vicinity of the ROI (e.g. an area twice the size of the ROI surrounding the ROI.), or the standard deviation of the activity outside of the ROI.

In step 912, a decision is made as to whether the ROIs satisfy localization criteria. If the ROIs satisfy the localization criteria, a user is alerted as indicated in step 914. If the localization criteria are not met by the initial analysis of the subdivided image, the threshold technique may be run using an alternative algorithm or an incremented subdivision size or threshold value. Step 916, e.g., indicates incrementing of the threshold value in one embodiment of the present invention. If the threshold technique is to be run using our alternative algorithm or an incremented subdivision size or threshold value, the process starts calculating the statistical quality of image in step 904. If no change is made to the algorithm used or the subdivision size or threshold value, no further action is taken as indicated in step 918.

The image data is typically characterized by low count rates in many of the intended clinical settings. Thus brief image acquisitions of one second or less are typically characterized as having low statistics.

Figure 10:
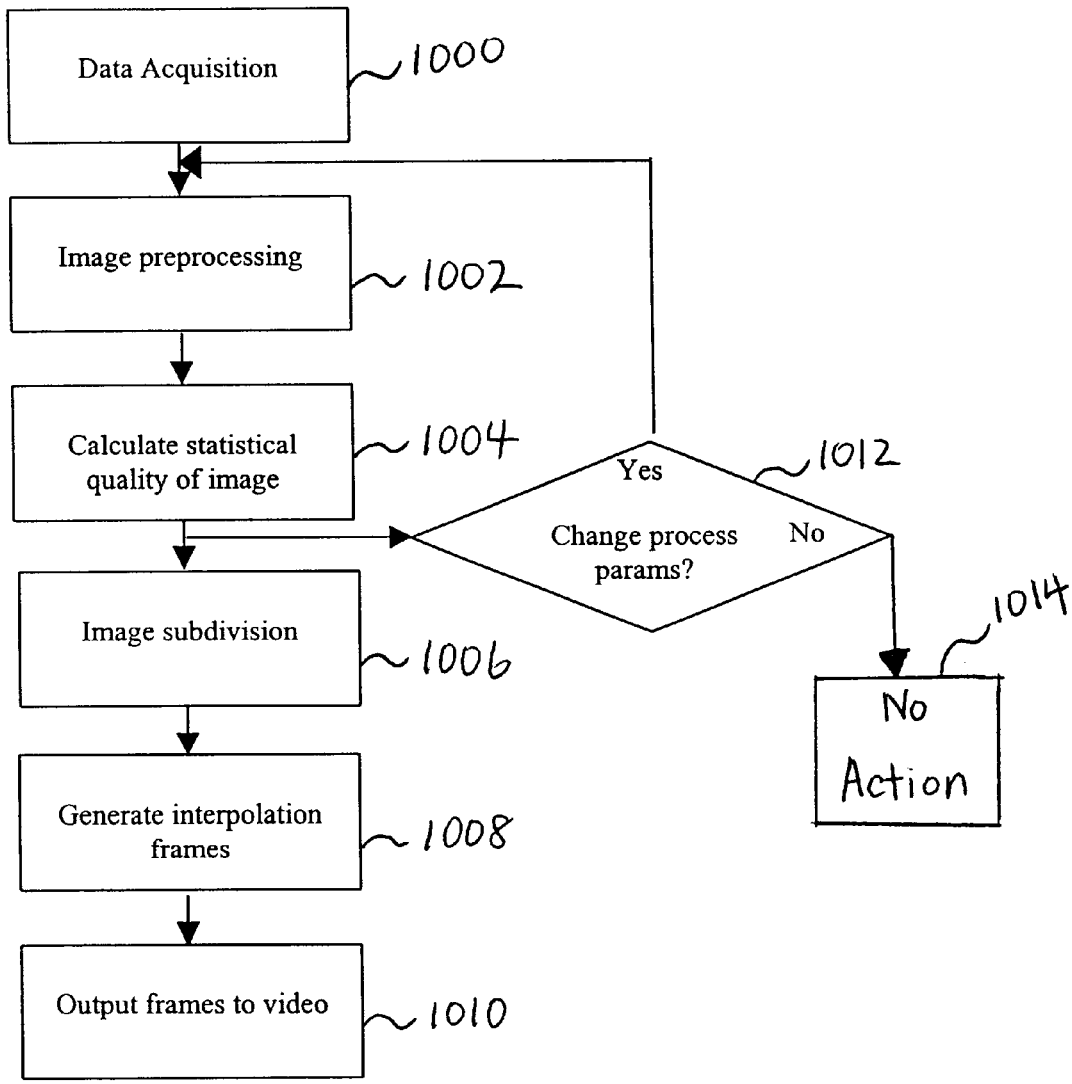
FIG. 10 is a flow diagram illustrating generation of statistically significant video from low statistic image data.

FIG. 10 is a flow diagram illustrating generation of statistically significant video from low statistic image data in one embodiment of the present invention.

The purpose of the described algorithm is to generate statistically significant video from the low statistic image data. This video output is then displayed.

Steps of Data Acquisition 1000, Image Preprocessing 1002 calculation of statistical quality of the image 1004 and Image Subdivision 1006 are similar to the steps 900, 902, 904 and 906 in FIG. 9.

If process parameters are to change after calculating statistical quality of image in step 1004, they preferably are changed in step 1012, and the steps of the flow diagram are re-performed starting with image processing in step 1002. If not, no action is taken as indicated in step 1014.

Further, in step 1008, the resulting images are mixed with the prior generated images by creation of frames that interpolate (or morph) the prior image with the new one. For example, if new image data are generated each 200 msec, and the video output is 60 frames per second, then there are approximately 12 video frames per acquired image frame. A slight delay (1 to 10 frames) in the output video stream allows one to morph the two images that are 200 msec apart over several (up to 12) frames in order to provide a less static image to the user to view. In step 1010, the frames are output as video.

The present invention in one embodiment may also include incorporation of an independent imaging detector system that is sensitive to beta particles but is relatively insensitive to gamma radiation. The beta particles typically are electrons emitted from the nuclei of certain isotopes. The detection requirements of photon radiation (x-rays and gamma-rays) is typically different than the detection requirements of massive particle radiations such as beta particles (or alpha particles or neutrons). Beta rays have a range on the order of millimeters in tissue so the beta detector in one embodiment is typically suited to localizing beta-labeled radio tracer only at the tissue surface. These differences allow the design of the portable imaging probe to be sensitive to either type of radiation independently. The designs of each detector typically are compatible with the integration of the two devices into a single probe capable of either gamma or beta detection, or both.

In one embodiment of the present invention, the beta detector preferably includes 300 μm to 1 mm wide strips of silicon. As such, it typically is transparent to gamma rays and so may be placed above the gamma detector without appreciable attenuation of the gamma rays. The beta detector is preferably held in place on a ceramic substrate, which also serves to hold the front end field-effect-transistors (FETs) or integrated amplification and processing electronics for the beta detector readout. The proximity of the front end FET to the detector allows a separation from this point to the remainder of the readout electronics, which are typically implemented in an ASIC on a board beneath the gamma detector. The ceramic holder for the beta detector may be a ring cutout in its center in order to not attenuate the gamma rays. Therefore, a gamma detector in one embodiment of the present invention preferably is sandwiched between the beta detector, which typically includes an array of detectors on silicon, and its readout electronics.

Having now described the invention in accordance with the requirements of the patent statutes, those skilled in this art will understand how to make changes and modifications in the present invention to meet their specific requirements or conditions. Such changes and modifications may be made without departing from the scope and spirit of the invention as set forth in the following claims.

What is claimed is:

1. A system to assess a distribution of x-ray, gamma ray, alpha ray or beta ray radiation emanating from radioisotope concentrated in human or animal tissue, the system comprising:

a portable imaging probe for imaging the distribution of x-ray, gamma ray, alpha ray or beta ray radiation emanating from the radioisotope concentrated in said human or animal tissue;

a display device for displaying the image of the distribution of x-ray, gamma ray, alpha ray or beta ray radiation emanating from the radioisotope concentrated in said human or animal tissue; and an audio device to generate an audio output to indicate a count rate corresponding to the distribution of x-ray, gamma ray, alpha ray or beta ray radiation emanating from the radioisotope concentrated in said human or animal tissue, while the image of the distribution of x-ray, gamma ray, alpha ray or beta ray radiation is being displayed on the display device.

2. The system of claim 1 further comprising:

a computer to process and store the distribution of radiation.

3. The system of claim 2 wherein the portable imaging probe is coupled to the computer via a cable.

4. The system of claim 2 wherein the portable imaging probe is coupled to the computer over a wireless communication medium.

5. The system of claim 2 wherein the portable imaging probe generates image data from the distribution of radiation, and wherein the system further comprises a software program that runs in the computer to process the image data.

6. The system of claim 5 wherein the software program variably segments one or more images represented by the image data.

7. The system of claim 1 wherein the display device displays a count of detected radiation.

8. The system of claim 1 wherein the portable imaging probe includes a collimator to direct the radiation.

9. The system of claim 8 wherein the collimator includes one or more chambers defined by chamber walls to direct the radiation.

10. The system of claim 9 wherein the chamber walls comprise a material having a high atomic number so as to limit septal penetration.

11. The system of claim 9 wherein the collimator has a pin hole aperture defined by the chamber walls.

12. The system of claim 11 wherein the portable imaging probe further includes an extension to couple to the collimator, and wherein the extension has an aperture smaller than the pin hole aperture.

13. The system of claim 8 wherein the collimator includes diverging chamber walls that are diverging in one or two dimensions.

14. The system of claim 8 wherein the collimator includes parallel chamber walls.

15. The system of claim 1 wherein the portable imaging probe includes an imaging sensor to detect the radiation.

16. The system of claim 15 wherein the portable imaging probe further includes a beta detection sensor, wherein the radiation includes gamma rays and beta rays, and wherein the imaging sensor is used to detect the gamma rays and the beta detection sensor is used to detect the beta rays.

17. The system of claim 1 wherein the portable imaging probe includes a packaging, wherein the packaging comprises an inert material.

18. A system to assess a distribution of radiation concentrated in human or animal tissue, the system comprising:

a portable imaging probe capable of imaging the distribution of radiation in said human or animal tissue, said portable imaging probe for application at an exposed surface of a body of a human or animal;

a display device capable of displaying the image of the distribution of radiation;

an audio device to generate an audio output to indicate a count rate of the radiation; and a second portable imaging probe, wherein the portable imaging probe and the second portable imaging probe are used to generate X, Y and Z coordinates of a radioactive node, and wherein the X, Y and Z coordinates are used for three-dimensional localization of the radioactive node.

19. A method of assessing a distribution of x-ray, gamma ray, alpha ray or beta ray radiation emanating from radioisotope concentrated in human or animal tissue, the method comprising:

imaging the distribution of x-ray, gamma ray, alpha ray or beta ray radiation emanating from the radioisotope concentrated in said human or animal tissue using a portable imaging probe;

displaying the image of the distribution of x-ray, gamma ray, alpha ray or beta ray radiation emanating from the radioisotope concentrated in said human or animal tissue; and generating an audio output to indicate a count rate corresponding to the distribution of x-ray, gamma ray, alpha ray or beta ray radiation emanating from the radioisotope concentrated in said human or animal tissue, while displaying the image of the distribution of x-ray, gamma ray, alpha ray or beta ray radiation.

20. The method of assessing a distribution of radiation of claim 19 further comprising:

varying the audio output to indicate sites of interest for measuring and displaying high quality images representative of the distribution of radiation.

21. The method of assessing a distribution of radiation of claim 20 wherein varying the audio output includes varying a tone of the audio output.

22. The method of assessing a distribution of radiation of claim 20 wherein varying the audio output includes varying a phase of the audio output.

23. The method of assessing a distribution of radiation of claim 20 wherein varying the audio output includes varying an intensity of the audio output.

24. The method of assessing a distribution of radiation of claim 20 wherein varying the audio output includes varying a stereo distribution of the audio output.

25. The method of assessing a distribution of radiation of claim 19 further comprising:

varying the audio output to indicate presence of one or more foci.

26. The method of assessing a distribution of radiation of claim 25 wherein varying the audio output includes varying a tone of the audio output.

27. The method of assessing a distribution of radiation of claim 25 wherein varying the audio output includes varying a phase of the audio output.

28. The method of assessing a distribution of radiation of claim 25 wherein varying the audio output includes varying an intensity of the audio output.

29. The method of assessing a distribution of radiation of claim 25 wherein varying the audio output includes varying a stereo distribution of the audio output.

30. The method of assessing a distribution of radiation of claim 19 further comprising:

using the image and the audio output to localize one or more sources of radiation.

31. The method of assessing a distribution of radiation of claim 19 further comprising:

displaying the count rate of the radiation.

32. The method of assessing a distribution of radiation of claim 19 further comprising processing the distribution of radiation to identify local concentrations of radiation.

33. The method of assessing a distribution of radiation of claim 32 wherein processing the distribution of radiation to identify local concentrations of radiation includes identifying regions of interest within the distribution of radiation.

34. The method of assessing a distribution of radiation of claim 33 wherein processing the distribution of radiation to identify local concentrations of radiation further includes entering input parameters to be used during the identification of the regions of interest.

35. The method of assessing a distribution of radiation of claim 33 wherein processing the distribution of radiation to identify local concentrations of radiation further includes evaluating each of the regions of interest to qualify it as a local concentration of radiation.

36. The method of assessing a distribution of radiation of claim 35 wherein each of the regions of interest is qualified as a local concentration of radiation when a standard deviation of the activity of the region of interest is below a predetermined value.

37. The method of assessing a distribution of radiation of claim 35 wherein each of the regions of interest is qualified as a local concentration of radiation when a ratio of an activity in the region of interest to a background activity is above a predetermined value.

38. The method of assessing a distribution of radiation of claim 32 wherein processing the distribution of radiation to identify local concentrations of radiation includes image preprocessing, the image preprocessing including processing the distribution of radiation to generate the image using triangulation techniques.

39. The method of assessing a distribution of radiation of claim 38 wherein processing the distribution of radiation to generate the image includes generating a raw image using the distribution of radiation.

40. The method of assessing a distribution of radiation of claim 39 wherein processing the distribution of radiation to generate the image further includes converting the raw image into the image using one or more processing tools.

41. The method of assessing a distribution of radiation of claim 38 wherein processing the distribution of radiation to identify local concentrations of radiation further includes calculating a statistical quality of the image.

42. The method of assessing a distribution of radiation of claim 38 wherein processing the distribution of radiation to identify local concentrations of radiation further includes subdividing the image.

43. The method of assessing a distribution of radiation of claim 42 wherein subdividing the image includes generating a lower resolution image.

44. The method of assessing a distribution of radiation of claim 43 wherein a resolution to which the image is reduced is determined on the basis of default parameters.

45. The method of assessing a distribution of radiation of claim 43 wherein a resolution to which the image is reduced is determined on the basis of parameters calculated using the image.

46. The method of assessing a distribution of radiation of claim 43 wherein a resolution to which the image is reduced is determined on the basis of user specified parameters.

47. The method of assessing a distribution of radiation of claim 42 wherein processing the distribution of radiation to identify local concentrations of radiation further includes image thresholding.

48. The method of assessing a distribution of radiation of claim 47 wherein image thresholding includes identifying regions of interest in the subdivided image using one or more pattern recognition algorithms.

49. The method of assessing a distribution of radiation of claim 47 wherein image thresholding includes incrementing a subdivision size when one or more regions of interest do not qualify as a local concentration of radiation using a current subdivision size.

50. The method of assessing a distribution of radiation of claim 47 wherein image thresholding includes using a new threshold value when one or more regions of interest do not qualify as a local concentration of radiation using a current threshold value.

51. The method of assessing a distribution of radiation of claim 19 wherein imaging the distribution of radiation includes using the portable imaging probe to scan said human or animal tissue in search of regions of interest.

52. The method of assessing a distribution of radiation of claim 51 wherein using the portable imaging probe to scan said human or animal tissue in search of regions of interest includes scanning the animal tissue in search of a sentinel node.

53. The method of assessing a distribution of radiation of claim 19 wherein generating and displaying an image includes generating a statistically significant video from low statistic image data.

54. The method of assessing a distribution of radiation of claim 53 wherein generating a statistically significant video includes generating interpolation frames, the interpolation frames being mixture between previously generated images and newly generated images.

\* \* \* \* \*